(12) United States Patent
Schwabe et al.

(10) Patent No.: US 8,545,483 B2
(45) Date of Patent: Oct. 1, 2013

(54) PHYSIOLOGICAL SENSORS WITH TELEMONITOR AND NOTIFICATION SYSTEMS

(75) Inventors: Jackie A. Schwabe, Milwaukee, WI (US); Chris Budish, Menomonee Falls, WI (US)

(73) Assignee: Honeywell International Inc., Morristown, NJ (US)

( * ) Notice: Subject to any disclaimer, the term of this patent is extended or adjusted under 35 U.S.C. 154(b) by 1264 days.

(21) Appl. No.: 11/684,959

(22) Filed: Mar. 12, 2007

(65) Prior Publication Data

US 2008/0228048 A1 Sep. 18, 2008

(51) Int. Cl.
*A61K 9/22* (2006.01)

(52) U.S. Cl.
USPC .............. 604/891.1; 604/64; 604/65; 604/66; 604/67

(58) Field of Classification Search
USPC ........................................... 604/891.1, 64–67
See application file for complete search history.

(56) References Cited

U.S. PATENT DOCUMENTS

| | | | |
|---|---|---|---|
| 2003/0212379 A1* | 11/2003 | Bylund et al. | 604/504 |
| 2004/0077995 A1* | 4/2004 | Ferek-Petric et al. | 604/66 |
| 2006/0079740 A1* | 4/2006 | Silver et al. | 600/309 |
| 2006/0263839 A1 | 11/2006 | Ward | |

* cited by examiner

*Primary Examiner* — Kevin C Sirmons
*Assistant Examiner* — Edelmira Bosques
(74) *Attorney, Agent, or Firm* — Husch Blackwell

(57) ABSTRACT

Systems and methods are provided which enable communications to be initiated locally relative to an individual's developing physiological condition and remotely as the condition requires. Physiological sensors and associated medical delivery systems can be coupled to a unit wearable by an individual which can provide various audible or visual outputs and one or more manual inputs indicative of the individual's condition. A global positioning unit can be incorporated so that condition information as well as location information can automatically be provided, wirelessly, to a remote monitoring system for follow up as needed.

15 Claims, 2 Drawing Sheets

PHYSIOLOGICAL SENSORS WITH TELEMONITOR AND NOTIFICATION SYSTEMS

FIELD

The invention pertains to systems and methods for monitoring physiological conditions of individuals. More particularly, the invention pertains to such systems and methods which incorporate one or more physiological sensors coupled to a wireless communications interface, which is also receptive of manual inputs to either intermittently or continuously communicate parametric information pertaining to analytes.

BACKGROUND

It has been recognized that there are advantages in being able to couple partially or totally implanted physiological sensors to partially or totally implantable drug delivery systems. Representative sensors include those for monitoring glucose concentration, lactate concentrations, nitric oxide or metabolytes thereof or the like. Delivery systems including partially or fully implantable insulin pumps or the like which can be driven directly or indirectly off of various sensor outputs.

There are times where the respective individual may be suffering from one or more out of range analyte concentrations. It would be desirable to be able to address these circumstances promptly. For example, where an individual is a diabetic and regularly receiving insulin, it would be useful to be able to promptly inform the person relative to an out of range glucose concentration. It would also be desirable to be able to monitor such information from a displaced, remote location.

There thus continues to be outstanding needs to be able to inform individuals as to various of their analyte concentrations. It would also be desirable to provide a vehicle that would enable such individuals to respond to such notices or information.

DETAILED DESCRIPTION

Figure 1:
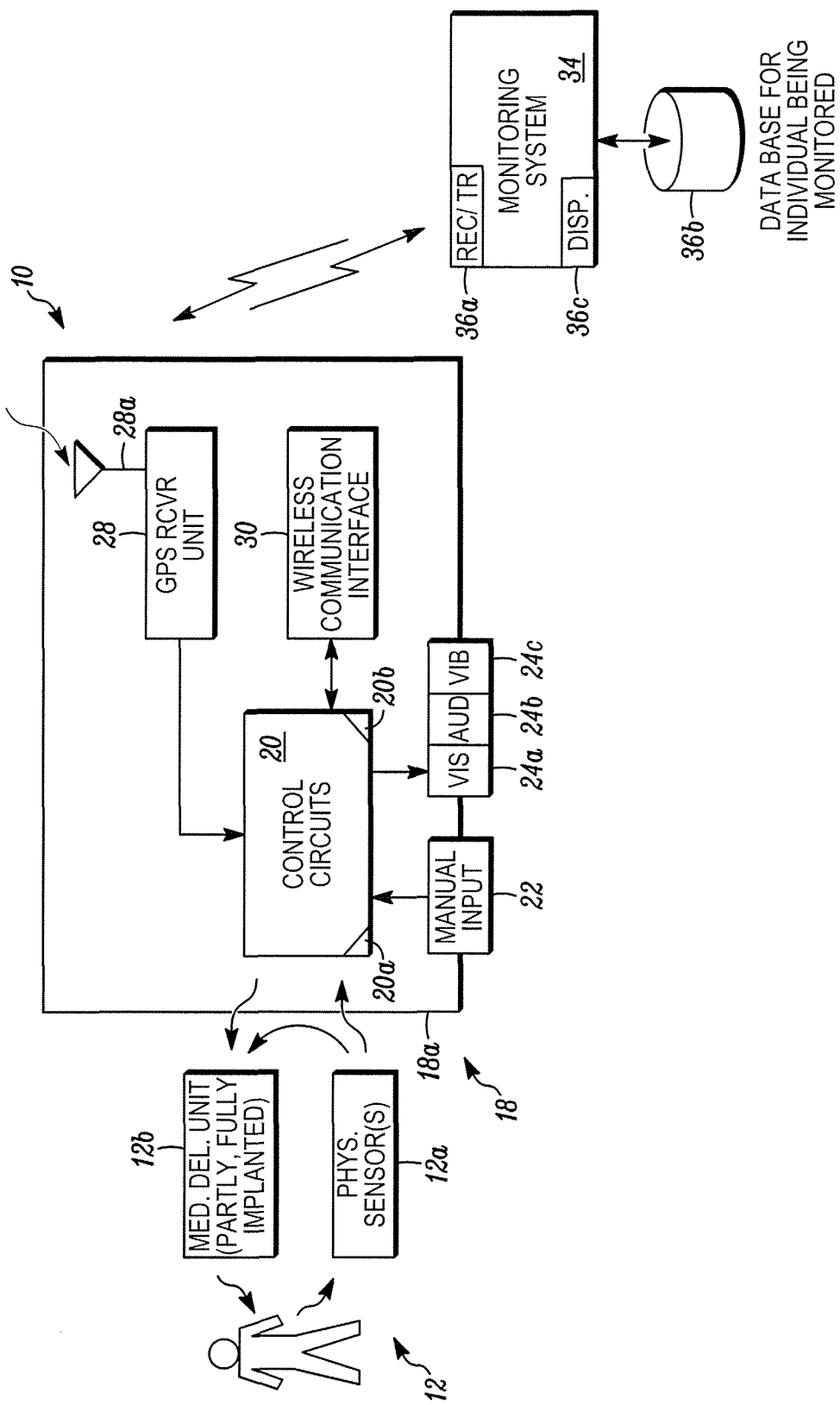
FIG. 1 is a block diagram of a system in accordance with the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In one embodiment of the invention, signals or information from a physiological sensor, such as a glucose sensor, which might be partially or fully implanted in an individual, can be coupled to a unit worn or carried by the individual. In accordance with the invention, the unit can incorporate circuitry to respond to signals received from the respective sensor or sensors and to notify the individual locally, either visually, audibly or by vibration as to measured glucose concentrations. In one aspect of the invention, a manual input can be provided, such as a push button or the like, where the respective individual can respond to concentration information. Such information, for example, might indicate an out of range concentration. The user's response could activate a drug delivery system such as an insulin delivery system as well as to substantially automatically communicate with a displaced monitoring system.

In one aspect of the invention, the unit can incorporate a GPS location device to automatically provide location information to the remote monitoring system in the event that a medical intervention is necessary on an emergency basis.

In accordance with a method which embodies the invention, a medical professional monitoring the outputs received from the displaced individual could respond to parameter variations, such as out of range glucose concentrations, to contact relatives, friends, emergency medical teams and the like, for example if the individual has failed to respond by activating the manual input. The individual's location based on GPS data received from the unit can be provided either to pre-designated contacts or an emergency medical response team.

FIG. 1 illustrates a system 10 which embodies the present invention. As illustrated in FIG. 1, a drug delivery system 12 which can incorporate one or more physiological sensors 12a and one or more medication delivery devices 12b is associated with a particular individual. The sensors 12a and delivery unit 12b can be partially or fully implanted into the individual. Alternately, the sensors can be external of the individual.

The sensors 12a and delivery unit 12b can be coupled either on a wired or wireless basis as would be understood by those of skill in the art. Representative sensors include those that respond to glucose, lactate, glutamate, potassium or dopamine all come within the spirit and scope of the present invention. Neither the nature of the analyte, nor the details of respective sensors or delivery systems are limitations of the present invention.

The respective individual can carry or wear a communications unit 18 which includes a housing 18a. The unit 18 can be in wired or wireless communication with either or both of the physiological sensor(s) 12a or medication delivery unit 12b without limitation.

Communication unit 18 can include control circuitry 20 which might be implemented with one or more programmable processors 20a and local control software 20b as would be understood by those of skill in the art. Unit 18 can include one or more manual inputs 22 which could be implemented as push buttons, slide switches or the like to enable the user or wearer of the communications unit 18 to respond to one or more visual outputs presented on a display device 24a, audible or verbal outputs which could be presented on a speaker 24b, as well as vibratory outputs from a vibrator 24c.

Unit 18 can also incorporate a global positioning system (GPS) unit 28 and associated antenna 28a which can automatically provide location information to control circuits 20. Unit 18 can also include a wireless interface 30, for example an interface to one or more local cellular telephone systems.

The wireless interface 30 enables unit 18 to wirelessly communicate with one or more remote or displaced monitoring systems 34. System 34 can include a wired or wireless communications receiver/transmitter 36a, a patient database 36b and one or more visual display devices which can present information via software driven graphical user interfaces 36c. Those of skill in the art will understand that the details of the monitoring system 34 do not represent limitations of the present invention. Medical professionals at the monitoring system 34 can respond to data from one or more sensors 12a received via interface 30 which are indicative of ongoing physiological conditions of the individual who is wearing or carrying unit 18. Control circuits 20 can communicate with the individual via output devices 24a, b and c to indicate an out of range value of an analyte being measured. The individual can respond via manual input 22 which can in turn cause control circuits 20 to activate the delivery unit 12b to provide an additional dose of medication consistent with outputs from the sensor 12a. Additionally, information can be forwarded to monitoring system 34 as to condition of the individual, whether input 22 has been activated, as well as location.

Figure 2:
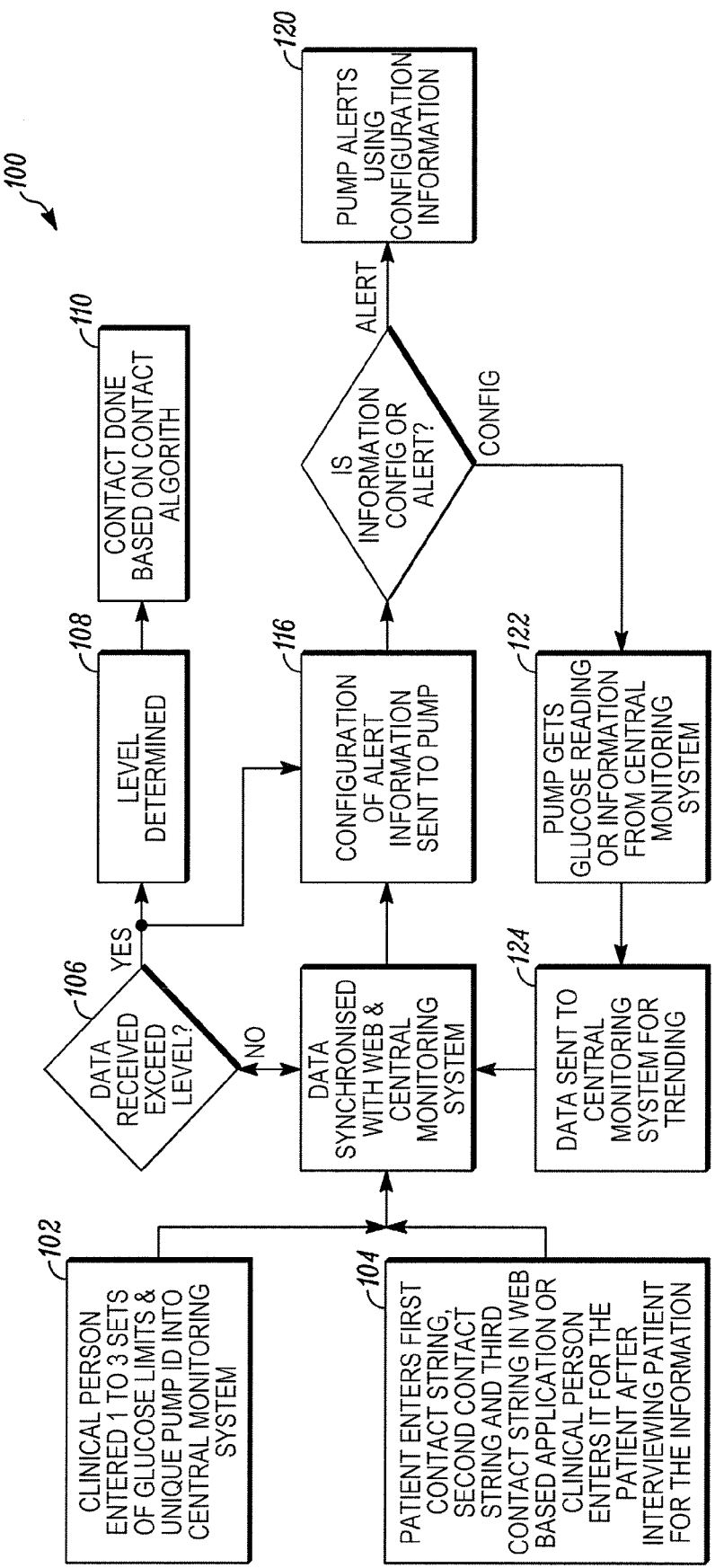
FIG. 2 illustrates a process in accordance with the invention.

FIG. 2 illustrates an exemplary method 100 which could be implemented at the monitoring system 34. As initial activities, a clinical or medical professional can have entered one or more sets of medication limits, such as glucose limits, and information associated with the delivery system 12b into database 36b associated with a monitoring system 34. Additionally, a plurality of contacts provided by the individual carrying the unit 18 can also be entered into the database 36b as at 104. Activities 102, 104 can be implemented via one or more web based software applications and associated graphical users' interfaces 36c.

An input via unit 18, indicative of an out of range value for one or more of the analytes being measured, can be received as at 106 at system 34. In response to a determined level, as at 108 one or more contacts can be initiated, as at 110, based on previously entered contact information. Additionally, commands or information can be coupled, as at 116, via unit 18 to the delivery system 12b. The incoming information can produce a local alert and/or activation of the delivery system 12b as at 120. The control circuits 20 can provide additional information received from sensor(s) 12a, as at 122, to record and present developing trends relative to the individual's condition.

One or more of the contacts 104, can intervene with the individual as needed. Alternately, an emergency medical team can be dispatched to check on the individual based on location information received from the GPS unit 28.

Those of skill in the art will understand that the method 100 contemplates multiple levels of contact relative to the individual using the unit 18. At one of the alert limits, the system 34 can attempt to contact the individual. After a pre-established period of time, if the person has not been reached or does not respond by using the manual input 22 then the next level of contact can be initiated. Additional levels of alarm limits can be established as at 104. System 34 can automatically move from the first contact level to the second contact level which could include contacting one or more persons previously designated as contacts, as at 104 or ultimately automatically contacting an emergency medical unit for intervention purposes.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. An apparatus comprising:
  a delivery device to deliver a medicinal solution to an individual;
  at least one sensor of a physiological condition of the individual; and
  a communication unit further comprising:
    a housing carried or worn by the individual;
    control circuits coupled to at least one of the delivery device or the sensor;
    location establishing circuitry coupled to the control circuits;
    at least one of an audible or visual output device coupled to the control circuits providing an audible or visual notification to the individual of an out of range physiological condition sensed by the at least one sensor;
    a manually operable input device disposed on a surface of the housing and coupled to the control circuits, the manually operable input device is activated by the individual in response to the out of range physiological condition and responsive thereto, causes the delivery device to deliver the medicinal solution to the individual; and
    an interface, coupled to the control circuits that automatically transmits to a displaced receiver, wirelessly, at least information relative to activation of the manually operable input device and the physiological condition of the individual.

2. An apparatus as in claim 1 where the control circuits couple information pertaining to the physiological condition of the individual and medicinal information to the interface for transmission to the receiver.

3. An apparatus as in claim 2 where the interface communicates with the receiver at least in part via a wireless telephone system.

4. An apparatus as in claim 1 which includes a monitoring system coupled to the receiver.

5. An apparatus as in claim 4 where the monitoring system maintains a pre-stored contact list for the individual.

6. An apparatus as in claim 5 where the monitoring system initiates multiple levels of contact relative to the individual until a desired contact is reached.

7. An apparatus as in claim 5 where the monitoring system includes a display device that visually presents the contact information in response to information pertaining to the physiological condition of the individual.

8. An apparatus in claim 7 where the monitoring system displays position related information received from the interface.

9. An apparatus as in claim 8 where the monitoring system responds to indicia associated with the manually operable input device.

10. An apparatus as in claim 9 where the control circuits respond to actuation of the input device to cause the delivery device to deliver a medicinal solution to the individual.

11. An apparatus as in claim 1 which includes circuitry that compares at least some of the information to at least a first range of values, and, responsive thereto, selecting a predetermined contact with whom to initiate a communication with a third part concerning the individual.

12. An apparatus as in claim 11 which includes circuits that establish trend information relative to outputs from the at least one sensor.

13. An apparatus as in claim 12 with the control circuits including at least one pre-stored range associated with an analyte of the individual, the control circuits activating the delivery device in response to analyte indicia from the sensor having a predetermined relationship to a pre-stored range, and, responding to a signal from the input device.

14. An apparatus as in claim 12 which includes circuits responsive to the trend information, that activate the delivery device to provide a medicinal fluid to the individual.

15. An apparatus as in claim 1 with the control circuits including at least one pre-stored range associated with an analyte of the individual, the control circuits activating the delivery device in response to analyte indicia from the sensor having a predetermined relationship to a pre-stored range, and, responding to a signal from the input device.

* * * * *